(12) United States Patent
Jenkner

(10) Patent No.: US 6,696,587 B2
(45) Date of Patent: Feb. 24, 2004

(54) PROCESS FOR TREATING AMINOSILANE DISCOLORATIONS

(75) Inventor: Peter Jenkner, Rheinfelden (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/234,385

(22) Filed: Sep. 5, 2002

(65) Prior Publication Data

US 2003/0042127 A1 Mar. 6, 2003

(30) Foreign Application Priority Data

Sep. 5, 2001 (DE) .......................... 101 43 568

(51) Int. Cl.$^7$ .............................. C07F 7/10; C07B 63/00
(52) U.S. Cl. .................. 556/413; 204/158.21; 204/901; 204/902
(58) Field of Search ...................... 556/413; 204/158.21, 204/901, 902

(56) References Cited

U.S. PATENT DOCUMENTS 4,234,502 A 11/1980 Kappler et al.

FOREIGN PATENT DOCUMENTS

| DE | 25 21 399 A1 | 11/1976 |
|---|---|---|
| EP | 0 464 819 A1 | 1/1992 |
| EP | 0 702 017 A1 | 3/1996 |

OTHER PUBLICATIONS

Patent Abstracts of Japan, JP 56–104891, Aug. 20, 1981.

*Primary Examiner*—Samuel Barts
(74) *Attorney, Agent, or Firm*—Oblon, Spivak, McClelland, Maier & Neustadt, P.C.

(57) ABSTRACT

A discoloration of an aminosilane having a content of a free base is treated by adding an acid chloride to the aminosilane to obtain a mixture having a molar excess of acid chloride; neutralizing the molar excess of the acid chloride in one or more steps with a molar deficit of a base to obtain a mixture containing a salt; separating off the salt from; and irradiating the remaining aminosilane with UV-containing light.

20 Claims, No Drawings

PROCESS FOR TREATING AMINOSILANE DISCOLORATIONS

BACKGROUND OF THE INVENTION

1. Field of the Invention

The invention relates to a process for treating a discoloration of an aminosilane.

2. Discussion of the Background

Organofunctional silanes are of great economic interest and currently envelop a multiplicity of industrial applications.

In particular 3-chloropropylchlorosilanes are important intermediates in the preparation of organofunctional silanes. They are generally prepared by hydrosilylation of allyl chloride. 3-Chloropropyltrichlorosilane or 3-chloropropylmethyldichlorosilane can be used to prepare, for example, 3-chloro-propyltrialkoxysilanes, 3-chloropropylmethyldialkoxysilanes and 3-aminopropyltrialkoxysilanes, such as 3-aminopropyltrimethoxysilane (AMMO) or 3-aminopropyl-triethoxysilane (AMEO); 3-aminopropylmethyldialkoxysilanes; N-aminoethyl-3-aminopropyltrialkoxysilanes, such as N-aminoethyl-3-aminopropyltrimethoxysilane (DAMO), N-aminoethyl-3-aminopropylmethyldialkoxysilanes and 2-aminoethyl-2-N'-aminoethyl-3-N-aminopropyl-trialkoxysilane. The aminosilanes can be high-purity products or technical quality grades. Thus, technical quality grades also include, for example, oligomeric aminosilane fractions. The term aminosilanes thus also comprises mixtures of identical or different monomeric aminoalkoxysilanes and their oligomers and polymers in weight ratios of 0.5:99.5 to 99.5:0.5. In addition said technical quality grades of aminosilanes can also comprise what are termed bis-aminosilanes.

In addition, aminosilanes which are obtained in the manner described above generally further have an unwanted content of hydrolyzable and non-hydrolyzable chloride. The hydrolyzable chloride is also termed acid chloride.

In addition, in the case of aminosilanes, a discoloration is frequently observed which reduces the quality and restricts the potential uses for such products. Such discolorations can arise, for example, by photooxidation.

DE-A 25 21 399 discloses a process for preparing aminoalkylsilanes in which a haloalkylsilane is reacted with excess ammonia. An amount of metal alkoxide, which may be dissolved in alcohol, for example sodium methoxide in methanol, which is equivalent to the amount of chloride present in the mixture is added to the mixture produced in the amination, after filtration. In the course of everyday operations, overtitration is easily possible, so that an excess of base remains in the product.

EP-A 0 702 017 teaches removing hydrolyzable chloride from aminoorganosilanes by a targeted substoichiometric procedure using a metal alkoxide and a product-sparing working temperature.

However, to neutralize acid chloride in aminosilanes, other basic compounds can also be used, for example alkali metal or alkaline earth metal, alkali metal hydroxides or alkaline earth metal hydroxides, alkali metal carbonates or alkaline earth metal carbonates, acid or neutral or basic salts (EP-A 0 464 819), metal oxides or clay earths.

SUMMARY OF THE INVENTION

It is an object of the present invention to provide a method for reducing the discoloration of aminosilanes.

This and other objects have been achieved by the present invention the first embodiment of which includes a process for treating a discoloration of an aminosilane, comprising:
- adding an acid chloride to said aminosilane having said discoloration to obtain a mixture having a molar excess of said acid chloride;
- neutralizing said molar excess of said acid chloride in one or more steps with a molar deficit of a base to obtain a mixture containing a salt of said acid chloride and said base;
- separating off said salt from said mixture containing said salt to obtain a treated aminosilane; and
- irradiating said treated aminosilane with UV-containing light to obtain an irradiated aminosilane.

DETAILED DESCRIPTION OF THE INVENTION

Surprisingly it has been found by the present inventors that an already discolored aminosilane which is obtainable by reacting a chloroalkylsilane with ammonia or an organic amine and which has a content of a free base can be decolorized by adding a molar excess of acid chloride to the aminosilane. The free base in the aminosilane can be an alkali metal alkoxide, alkali metal hydroxide or alkaline earth metal hydroxide, for example, but not exclusively, sodium methoxide, potassium ethoxide, sodium hydroxide, potassium hydroxide or magnesium hydroxide. The aminosilane has a content of free base due to neutralization of hydrolyzable chloride, namely acid chloride, in the product with a free base, for example, an alkali compound. The discoloration of the aminosilane is due to an oxidation, in particular, photo-oxidation in the presence of sufficient amounts of oxygen. The discolored aminosilane can be decolorized in a simple and economic manner if acid chloride, for example hydrogen chloride, ammonium chloride or trimethylchlorosilane, is added to the aminosilane so that there is an excess of acid chloride in the aminosilane. The excess acid chloride is neutralized in one or more steps with a molar deficit of a free base, for example an alkali metal alkoxide, an alkali metal hydroxide or an alkali metal carbonate.

The resultant salt is separated off, in which case preferably an acid chloride content of >6 ppm by weight, in particular a content between the limit of detection for acid chloride and <50 ppm by weight, remains in the product. Thus, after the neutralization there is no free base in the product. Any free alcohol present is distilled off and the aminosilane is irradiated with UV-containing light. Preferably the process according to the present invention is carried out under inert gas, the inert gas containing less than 5000 ppm by weight of oxygen, preferably 0.001 to 4000 ppm by weight of oxygen. The amount of oxygen in the inert gas includes all values and subvalues therebetween, especially including 0.005, 0.01, 0.05, 0.1, 0.5, 1.5, 10, 50, 100, 500, 1000, 1500, 2000, 2500, 3000 and 3500 ppm. Preferably, the treated product is stored in the absence of oxygen, for example blanketed under an inert gas. Preferably the inert gas used is nitrogen or argon.

The present invention therefore relates to a process for treating a discoloration of an aminosilane. The aminosilane is obtainable by reacting a chloroorganosilane with ammonia or an organic amine and has a content of a free base. The treatment of discoloration comprises adding acid chloride to the aminosilane so that there is an excess of acid chloride in the aminosilane, neutralizing the excess acid chloride in one or more steps with a deficit of a free base, separating off the salt and irradiating the aminosilane with UV-containing light.

In the method of the present invention the base preferably used is alkali metal alkoxide, alkali metal hydroxide or alkali metal carbonate. The base can be used as a solid, for example pulverulent, dispersed or dissolved in solvents, for example in a water-soluble organic solvent such as dimethylformamide (DMF), tetrahydrofuran (THF), alcohol, aldehyde, ketone or a mixture thereof.

Preferably, the treatment is carried out at a temperature of from 0 to 100° C., particularly preferably at a temperature of from 25 to 60° C., very particularly preferably at a temperature of from 30 to 40° C. The treatment temperature includes all values and subvalues therebetween, especially including 10, 20, 30, 40, 50, 60, 70, 80 and 90° C.

It is further preferred that, in the process of the present invention, the base-free aminosilane or the hydrolyzable chloride-containing aminosilane is irradiated and preferably the UV source used for the irradiation emits light of a wavelength of at least 200 nm, more preferably the UV-light has a wavelength of from 200 to 400 nm. In particular, UV sources of 500 W to 2 kW of commercial design are used. The energy of the UV source includes all values and subvalues therebetween, especially including 600, 700, 800, 900, 1000, 1100, 1200, 1300, 1400, 1500, 1600, 1700, 1800 and 1900 W.

Preferably, UV-light of a wavelength of 200 to 400 nm is used for the irradiation, particularly preferably light of a wavelength of from 250 to 300 nm, most particularly preferably light of a wavelength of 254 nm. The wavelength of the UV-light includes all values and subvalues therebetween, especially including 220, 240, 260, 280, 300, 320, 340, 360, and 380 nm.

Preferably, the irradiation is carried out at a product temperature of 10 to 60° C., in particular 20 to 40° C., over a period of 2 to 60 hours, preferably 4 to 24 hours. The product temperature during irradiation includes all values and subvalues therebetween, especially including 20, 30, 40 and 50° C. The irradiation time includes all values and subvalues therebetween, especially including 5, 10, 15, 20, 25, 30, 35, 40, 45, 50 and 55 hours.

Particularly preferably, the irradiation is carried out under an essentially oxygen-free inert gas blanketing, in particular under argon or nitrogen of the above-mentioned quality.

According to the present invention, preferably aminosilanes of the general formula I are treated

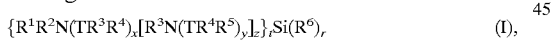
$$\{R^1R^2N(TR^3R^4)_x[R^3N(TR^4R^5)_y]_z\}_t Si(R^6)_r \qquad (I),$$

wherein $R^1$ to $R^5$ are identical or different and are each hydrogen; a unbranched or branched $C_1$ to $C_8$ alkyl group optionally having at the terminals further organofunctional groups, such as OH, COOH, SH, $NO_2$ or organofunctional groups bound via divalent to hexavalent elements except carbon; a $C_3$ to $C_8$ cyclic alkyl group optionally having further organofunctional groups, such as OH, COOH, SH, $NO_2$ or organofunctional groups bound via divalent to hexavalent elements except carbon; an aryl group optionally containing, as heteroatoms, divalent to hexavalent elements, $R^6$ is a $C_1$ to $C_{18}$ alkyl or alkoxy group or a siloxy group, T is selected from the group of divalent to hexavalent elements of the Periodic Table of the Elements, in particular C, Si, O or S, and $1 \leq y \leq 20$, $1 \leq x \leq 20$, $0 \leq z \leq 20$, $1 \leq t \leq 3$, $r = 4 - t$.

Very particularly preferably, the aminosilanes used are the aminoalkylalkoxysilanes mentioned at the outset, for example, 3-aminopropyltrimethoxysilane (AMMO) or 3-aminopropyl-triethoxysilane (AMEO).

Generally, the process of the present invention is carried out by treating a discolored aminosilane, for example having a color index of around 15 Gardner (G), under inert gas which is generally essentially free from oxygen, except for the above-mentioned contents. The color index of the aminosilane can be at least 1, preferably at least 5 and most preferably at least 15G. The aminosilane is admixed with an acid chloride, so that a significant amount of acid chloride of $\leq 5000$ ppm by weight, preferably $\leq 1000$ ppm by weight, may be found in the resulting mixture. The mixture is neutralized by adding a substoichiometric amount of base, so that preferably <50 ppm, more preferably <25 ppm and most preferably <10 ppm by weight of acid chloride are present in the product. The resultant salt is separated off, for example by filtration or centrifugation. Optionally, free alcohol that is present can then be removed from the product under inert gas and at a temperature as gentle to the product as possible, preferably <80° C., more preferably <60° C., most preferably <40° C., for example by distillation under reduced pressure. The product is then irradiated with UV light. The process of the present invention can be carried out either continuously or batchwise.

An aminosilane thus treated according to the present invention is a clear, generally low-viscosity liquid and is distinguished by an outstandingly low color index, for example <2 G, in particular $\leq 1$ G, and an (acid) chloride value of <50 ppm by weight, preferably <25 ppm by weight and most preferably <10 ppm by weight.

German patent application 10143568.1 filed Sep. 5, 2001, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A process for treating a discoloration of an aminosilane, comprising:

adding an acid chloride to said aminosilane having said discoloration to obtain a mixture having a molar excess of said acid chloride;

neutralizing said molar excess of said acid chloride in one or more steps with a molar deficit of a base to obtain a mixture containing a salt of said acid chloride and said base;

separating off said salt from said mixture containing said salt to obtain a treated aminosilane; and irradiating said treated aminosilane with UV-containing light to obtain an irradiated aminosilane.

2. The process according to claim 1, wherein said aminosilane having said discoloration is obtainable by reacting a chloro-organosilane with ammonia or an organic amine; and wherein said aminosilane having said discoloration has a content of a free base.

3. The process as claimed in claim 1, which is carried out under an inert gas atmosphere; and wherein said inert gas contains <5000 ppm by weight of oxygen.

4. The process as claimed in claim 3, wherein said inert gas is nitrogen or argon.

5. The process as claimed in claim 1, wherein the base is an alkali metal alkoxide, an alkali metal hydroxide or an alkali metal carbonate.

6. The process as claimed in claim 1, wherein said UV-containing light is generated by a light source that emits light of a wavelength of at least 200 nm.

7. The process as claimed in claim 1, wherein said UV-containing light is generated by a light source having an output of 500 W to 2 kW.

8. The process as claimed in claim 1, wherein said UV-containing light has a wavelength of 200 to 400 nm.

9. The process as claimed in claim 1, wherein said irradiating is carried out at a temperature of said treated aminosilane of from 10 to 60° C.

10. The process as claimed in claim 1, further comprising heating said treated aminosilane to a temperature of from of 10 to 60° C.

11. The process as claimed in claim 1, wherein said irradiating lasts 2 to 60 hours.

12. The process as claimed in claim 1, wherein said adding and said neutralizing are carried out at a temperature in the range from 0 to 100° C.

13. The process as claimed in claim 1, wherein said base is in the form of a solid.

14. The process as claimed in claim 1, wherein said base is dissolved in a solvent selected from the group consisting of dimethylformamide, tetrahydrofuran, an alcohol, an aldehyde, a ketone and mixtures thereof.

15. The process as claimed in claim 1, wherein said aminosilane has the following formula

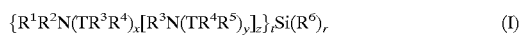 (I)

wherein $R^1$ to $R^5$ are identical or different and wherein $R^1$ to $R^5$ are each hydrogen, a $C_1$ to $C_8$ alkyl group, a $C_3$–$C_8$ cyclic alkyl group, an aryl group optionally having a heteroatom;

wherein $R^6$ is a $C_1$ to $C_{18}$ alkyl, a $C_1$ to $C_{18}$ alkoxy group or a siloxy group;

wherein T is selected from the group of divalent to hexavalent elements of the Periodic Table of the Elements;

wherein $1 \leq y \leq 20$;

wherein $1 \leq x \leq 20$;

wherein $0 \leq z \leq 20$;

wherein $1 \leq t \leq 3$; and wherein $r = 4-t$.

16. The process as claimed in claim 1, wherein said aminosilane is an aminoalkylalkoxysilane.

17. The process as claimed in claim 1, wherein said aminosilane is 3-aminopropyltrimethoxysilane or 3-aminopropyl-triethoxysilane.

18. The process as claimed in claim 1, wherein said aminosilane having said discoloration has a color index of at least 1G.

19. The process as claimed in claim 1, wherein said mixture having a molar excess of said acid chloride contains an amount of acid chloride of $\leq 5000$ ppm by weight.

20. The process as claimed in claim 1, wherein said irradiated aminosilane contains <50 ppm by weight of acid chloride.